US005166199A

United States Patent [19]

Kasch et al.

[11] Patent Number: 5,166,199

[45] Date of Patent: Nov. 24, 1992

[54] 11β-ARYL-16α,17α-CYCLOHEXANO-ESTRA-4,9-DIENES

[75] Inventors: Helmut Kasch; Gudrun Bertram; Anatoli Kurischko; Kurt Ponsold, all of Jena, Fed. Rep. of Germany

[73] Assignee: Schering Aktiengesellschaft, Berlin and Bergkamen, Fed. Rep. of Germany

[21] Appl. No.: 567,362

[22] Filed: Aug. 15, 1990

[51] Int. Cl.[5] ........................ C07J 53/00; C07J 75/00; A61K 31/58; A61K 31/575

[52] U.S. Cl. .................................... 514/169; 514/177; 514/178; 540/15; 552/514

[58] Field of Search ............... 552/514, 603, 605, 608; 514/177, 179, 169, 178; 540/15

[56] References Cited

FOREIGN PATENT DOCUMENTS

| | | | |
|---|---|---|---|
| 251142 | 11/1987 | German Democratic Rep. | 552/514 |
| 277684 | 4/1990 | German Democratic Rep. | 552/514 |
| 277685 | 4/1990 | German Democratic Rep. | 552/514 |

OTHER PUBLICATIONS

Neef, et al, Chemical Abstracts vol. 104, 1986, Abstract 34230f.

*Primary Examiner*—Robert T. Bond
*Assistant Examiner*—E. C. Ward
*Attorney, Agent, or Firm*—Millen, White & Zelano

[57] ABSTRACT

11⊕-Aryl-16α,17α-cyclohexano-estra-4,9-dienes of formula wherein $R^1$ is H or a methyl group;

$R^2$ is $-OCH_3$, $-SCH_3$, $-N(CH_3)_2$, $-NHCH_3$, $-CN$, $-CHO$, $-COCH_3$ or $-CHOHCH_3$;

X is $-CHO$, $-COCH_3$, $-CH_2OH$, $-CHOHCH_3$, $-CH_2CHO-C_{1-7}$-alkyl, $-CH_2CHO-C_{1-7}$-alkanoyl, $-CH_2O-C_{1-7}$-alkyl, $-CH_2O-C_{1-7}$-*alkanoyl*, $-COO-C_{1-7}$-alkyl, $CH_3CH_2-$, $-CH_3$, $-COOH$ or $-CN$; and Y is $=O$, $=NOH$, $=NOCH_3$ or a cyclic thioketal having 2 or 3 ring atoms are provided, as well as pharmaceutical compositions containing said compounds, methods of use of said compounds, and processes for their production.

11 Claims, No Drawings

11β-ARYL-16α,17α-CYCLOHEXANO-ESTRA-4,9-DIENES

This invention relates to 11beta-aryl-16alpha,17alpha-cyclohexano-estra-4,9-dienes of general formula I (I)

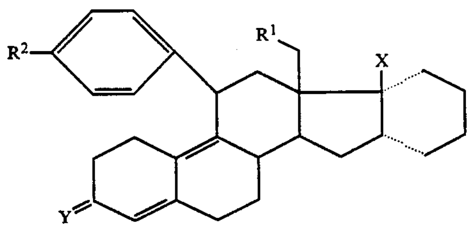

in which $R^1$ is a hydrogen atom or a methyl group, $R^2$ means $OCH_3$, $SCH_3$, $N(CH_3)_2$, $NHCH_3$, CN, CHO, $COCH_3$, $CHOHCH_3$, X means CHO, $COCH_3$, $CH_2OH$, $CHOHCH_3$, $CH_2CHO$ alkyl, $CH_2CHO$ alkanoyl, $CH_2O$ alkyl, $CH_2O$ alkanoyl, COO alkyl, and alkyl and alkanoyl means a carbon chain with 1 to 7 C atoms, $CH_3CH_2$, $CH_3$, COOH, CN and Y=O, NOH, $NOCH_3$ or a cyclic theoketal with 2 or 3 C ring atoms.

Preferably in the compounds of general formula I $R^1$ means a hydrogen atom, $R^2$=$OCH_3$, $N(CH_3)_2$, CHO or $COCH_3$ and X=CHO, $COCH_3$, $CH_2OH$ or $CHOHCH_3$ and Y means an oxygen atom or the hydroxyimino grouping NOH. The following compounds are especially preferred:

16alpha,17alpha-cyclohexano-11beta-(4-methoxyphenyl)-19-norpregna-4,9-diene-3,20-dione, 16alpha,17alpha-cyclohexano-11beta-(4-dimethylaminophenyl)-19-nor-pregna-4,9-diene-3,20-dione, 16alpha,17alpha-cyclohexano-20beta-hydroxy-11beta-(4-methoxyphenyl)-19-nor-pregna-4,9-diene-3,20-dione, 16alpha,17alpha-cyclohexano-11-beta-(4-dimethylaminophenyl)-20beta-hydroxy-19-nor-pregna-4,9-diene-3,20-dione, 16alpha,17alpha-cyclohexano-17beta-hydroxymethyl-11beta-(4-methoxyphenyl)-estra-4,9-dien-3-one, 16alpha,17alpha-cyclohexano-11beta-(4-dimethylaminophenyl)-17-beta-hydroxymethyl-estra-4,9-dien-3-one, 11beta-(4-acetylphenyl)-16alpha,17alpha-cyclohexano-17beta-hydroxymethyl-estra-4,9-dien-3-one, 16alpha,17alpha-cyclohexano-11beta-(4-dimethylaminophenyl)-17-beta-formyl-estra-4,9-dien-3-one.

The compounds according to general formula I have a strong affinity for the gestagen receptor, without themselves developing gestagen activity. They are competitive antagonists of progesterone (antigestagens). In the first place, the compounds according to the invention can be used for treatment of endocrine hormone-dependent tumors such as, e.g., breast cancer and meningioma but also for treatment of endometriosis and dysmenorrhea.

Since the compounds of general formula I displace from the receptor the progesterone necessary for maintenance of pregnancy, besides the already mentioned indications they are also suitable for triggering abortions and for inducing labor.

Besides, the determination of the affinity for the progesterone receptor, the abortive action of the substances, determined by animal experiments, serves for characterizing the antigestagen action.

The abortive action was determined on female pregnant rats (positive sperm detection—1st day of pregnancy) weighing between 180 and 200 g of subcutaneous administration of the test compound, suspended in peanut oil, on the 5th to 8th day of pregnancy. After autopsy on the 20th day of pregnancy, the uteri were examined. In this case, the number of pregnant females and the average number of fetuses per pregnant animal were determined.

The inhibitory effect was calculated as follows:

$$He = \left(1 - \frac{x_V \cdot n_K}{n_V \cdot x_K}\right) \cdot 100(\%)$$

x = number of pregnant females
n = number of impregnated females
V = test group
K = control group

| Group Substance | Total dose (mg/animal/4 d) | N | Fertility inhibition absol. | rel. % |
|---|---|---|---|---|
| NMe2,17beta-COMe | 10 | 7 | 5 | 71 |
| NMe2,17beta-CH2OH | 10 | 5 | 4 | 80 |
| Controls | — | 6 | 0 | 0 |

The affinity for the progesterone receptor was examined by the competitive binding of the substance to be tested and a suitable [$^3$H] labeled progestin [$^3$H]-ORG 2058 on the receptor.

Uterus cytosol, fresh or frozen at −20° C., obtained from infantile rabbits (Neuseelaender, Deutsche Riesen) 1 week after 5-day priming with estradiol benzoate (4×5 mg and 1×10 mg) was used as biological material. The cytosol concentration in the test corresponded to 20 mg of tissue/ml of incubation volume. The incubation was 20 hours at 0° C.

After adsorption of the free steroids by activated carbon/dextran and measurement of the protein-bound [$^3$H] in the supernatant, $I_{50}$ [?M] was determined as well as the relative binding affinity RBA, relative to the standard, progesterone.

$$RBA_{St.} = \left(\frac{I_{50}\ Prog.}{I_{50}\ St.}\right) \cdot 100[\%]$$

| Group Substance | RBA [%] |
|---|---|
| OCH3,17beta-COMe | 345 |
| NMe2,17beta-COMe | 470 |
| OCH3,17beta-CH2OH | 170 |
| NMe2,17beta-CH2OH | 220 |

The compounds of general formula I according to the invention can be used in the form of pharmaceutical preparations. The production of the preparations takes place according to methods of galenicals known in the art by mixing with organic or inorganic inert vehicles, which are suitable for enteral, percutaneous or parenteral application.

The dosage of the compounds according to the invention for said indications is between 1 and 1000 mg daily.

The compounds of general formula I are produced according to the invention in that a compound of general formula V

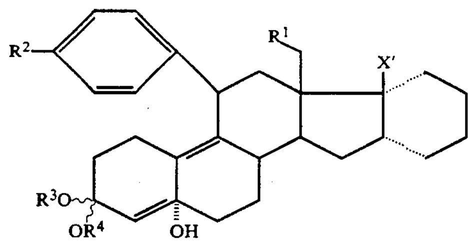

in which $R^1$ means a hydrogen atom or a methyl group and $R^3$ and $R^4$ each mean a methyl group or ethyl group or together mean an ethylene group or 2,2-dialkyklpropylene group, especially 2,2-dimethylpropylene group, as well as $R^{2'}$ and X' having the same meaning as $R^2$ and X in formula I, and optionally existing keto groups are protected, is converted, by acid treatment in a water-miscible solvent, into 11beta-aryl-16alpha,17alpha-cyclohexano-estra-4,9-dien-3-one of general formula I and then the latter is optionally derivatized to another compound of general formula I by acylation, aroylation, oxidation, thioketalization or oximation.

Aqueous acetic acid, p-toluenesulfonic acid or mineral acids such as hydrochloric acid, sulfuric acid, phosphoric acid or perchloroic acid are used as acids for the acid treatment and aqueous methanol, ethanol or acetone is used as solvent. Optionally it is heated to 60° C. to 70° C. during the acid treatment.

The further derivatizing takes place by oximation or thioketalization in the 3 position and with the presence of a 20 hydroxy group optionally by its acylation, aroylation or oxidation, and other compounds of general formula I according to the invention are used.

20 hydroxyethyl- or 20 hydroxymethyl-estra-4,9-dienes of general formula I are preferably acylated or aroylated in the presence of a pyridine base with an acid anhydride or acid chloride.

The thioketalization is performed with ethanedithiol or propanedithiol in the presence of a Lewis acid, preferably boron trifluoride etherate.

In the oxidation of the 20 hydroxy compounds to the corresponding ketones, aldehydes or acids, the operation is preferably performed with chromic acid in acetone (Jones oxidation) or else with pyridinium dichromate or pyridinium chlorochromate in methylene chloride under addition of sodium acetate and molecular sieve. In the production of 11beta-dimethylaminophenyl-estra-4,9-dienes the oxidation is performed preferably before introduction of the 11beta-aryl radical, after ketalization.

The oximation takes place with hydroxylamine hydrochloride or methoxyamine hydrochloride in alcohol solution in the presence of a base such as $Na_2CO_3$, $K_2CO_3$, dilute NaOH or KOH.

The production of the starting products of general formula V to be used according to the invention takes place according to the following diagram:

Lit. for II Patent specification DD 277685 A1 of Dec. 5, 1988 (H. Kasch, Ponsold, K. and Bertram, G.: Process for the production of 16alpha,17alpha-cyclohexano-estra-4,9-dien-3-ones) and patent specification DD 251142 A1 of Nov. 29, 1987 (K. Ponsold, Kasch, H, Kurischko, A., Stoelzner, W., Kamernitzky, A., Levina F. S., Nikitina, G., Korchow, W.: Process for the production of 16alpha,17alpha-cyclohexano-17-beta-acetyl-gonen-3-ones).

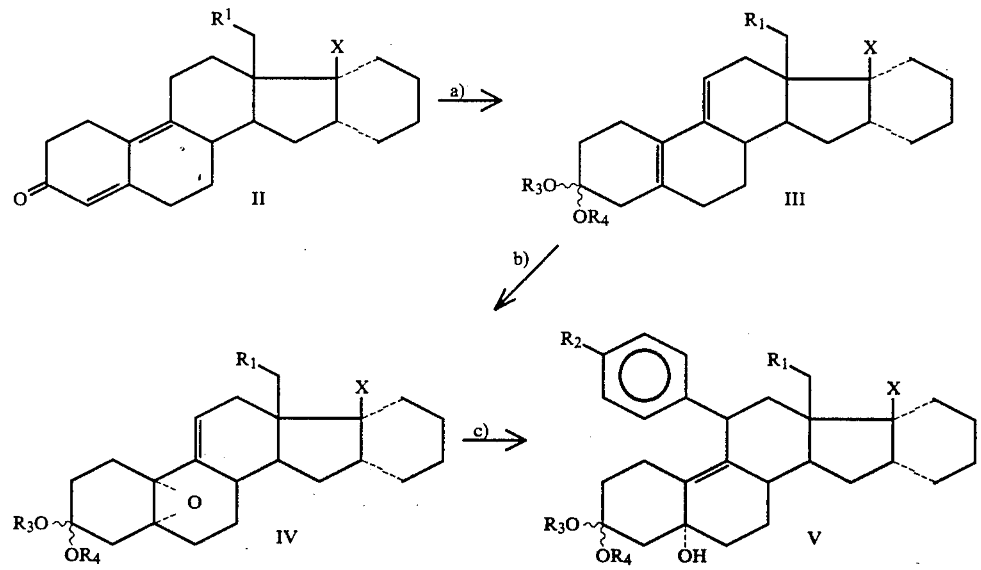

A start is made from 16alpha,17alpha-cyclohexano-estra-4,9-dienes II, which by ketalization to III and epoxidizing is first converted to 16alpha,17alpha-cyclohexano-5alpha,10alpha-epoxy-3-ketals IV and then by Grignardization with aryl magnesium halide in the presence of Cu(I) salts at a temperature of −30° C. to +30° C. is converted to 11beta-aryl-16alpha,17alpha-cyclohexano-5alpha-hydroxy-estr-9-enes V.

The ketalization is performed with an alcohol, preferably methanol, ethanol, ethylene glycol or 2,3-dimethyl propanediol in the presence of catalytic acid amounts, for example, of p-toluenesulfonic acid, sulfuric acid, oxalic acid or pyridinium tosylate and a dehydrating agent such as formic acid trimethyl ester or formic acid triethyl ester. Instead of orthoformic acid ester, advantageously boiling is performed on a water entrainer such as chloroform, benzene or toluene on a water separator.

In a preferred embodiment the epoxidizing is performed with a peracid, preferably m-chloroperbenzoic acid, perbenzoic acid or monoperphthalic acid, in a two-phase system consisting of an organic solvent, such as chloroform, methylene chloride, ether, benzene or toluene and a saturated aqueous sodium carbonate solution under vigorous stirring. A phenyl magnesium halide is used for the Grignardization, which contains in the p-position for the magnesium an $OCH_3$, $SCH_3$, $N(CH_3)_2$, $NHCH_3$, CN, $CH_3CHOH$, $CH(OR_4)$ group and in which halogen means bromine or chlorine. In this case, the operation is performed in a ether such as diethyl ether, tetrahydrofuran or dioxane, optionally under addition of a solubilizer such as for example, benzene or toluene. CuCN, CuO or CuCl are suitable as Cu(I) salt.

It was found that epoxidizing is surprisingly possible with a peracid when working in a two-phase system in the presence of an aqueous bicarbonate solution and a decomposition of the acid-sensitive 5alpha,10alpha epoxide is thus avoided.

The following examples serve for a more detailed explanation of the invention.

EXAMPLE 1 a)

16alpha,17alpha-Cyclohexano-3,3-ethylenedioxy-19-nor-pregna-5(10),9(11)-dien-20-one 0.9 g of 16alpha, 17alpha-cyclohexano-19-nor-pregna-4,9-dien-3-one after addition of 5 ml of glycol, 70 ml of benzene and 0.2 g of p-toluenesulfonic acid is boiled for 2 hours on a water separator. After completed reaction, it is mixed with bicarbonate solution and the steroid is extracted with benzene. The extracts, washed neutral with water, are concentrated by evaporation and crystallized from ether/n-hexane, and 0.92 g is obtained.

Mp: 124°-128° C. $[\alpha]_D$: 157°.

b)

16alpha,17alpha-Cyclohexano-3,3-ethylenedioxy-5alpha,10alpha-19-nor-pregna-5(10),9(11)-en-20-one 0.65 g of m-chloroperbenzoic acid is added, under vigorous stirring, to a suspension consisting of 1 g of 16alpha,17alpha-cyclohexano-3,3-ethylenedioxy-19-nor-pregna-5(10),9(11)-dien-20-one in 230 ml of methylene chloride and 20 ml of a saturated aqueous sodium carbonate solution. After completed reaction (15 minutes) the steroid is extracted with methylene chloride, the extracts are concentrated by evaporation and the remaining residue is flash-chromatographed on basic aluminum oxide (Greiz-Doelau) with toluene/ethyl acetate (14:1 to 9:1). After recrystallization from methanol, 0.4 g of 5alpha,10alpha-epoxide is obtained.

Mp: 170°-177° C.

c)

16alpha,17alpha-Cyclohexano-3,3-ethylenedioxy-5alpha-hydroxy-11beta-(4-methoxyphenyl)-19-nor-pregna-9-en-20-one 5 ml is taken from a 4-methoxyphenyl magnesium bromide solution prepared by reaction of 0.48 g of magnesium shavings and 2.36 ml of p-bromoanisole in 20 ml of tetrahydrofuran (THF) at 35° C. and mixed under argon cooling to −5° C. to −15° C. with 0.07 g of CuCl. It is stirred for 15 minutes with the cooling being maintained and then a solution of 0.3 g of 16alpha,17alpha-cyclohexano-3,3-ethylenedioxy-5alpha,10alpha-epoxy-nor-pregn-9(11)-en-20-one in 3 ml of THF is instilled. Then it is stirred for one hour at room temperature, then an aqueous ammonium chloride solution is added and the steroid is extracted with methylene chloride. After concentration by evaporation of the extracts, the residue is flash-chromatographed on basic aluminum oxide (Greiz-Doelau) with benzene/ethyl acetate (40:1). 0.297 g (78.5% of theory) of the 11beta-anisyl compound is obtained.

Mp: 152°-160° C. $[\alpha]_D$: 22.4°.

d)

16alpha,17alpha-Cyclohexano-11beta-(4-methoxyphenyl)-19-nor-pregna-4,9-diene-3,20-dione 0.2 g of 16alpha,17alpha-cyclohexano-3,3-ethylenedioxy-5alpha-hydroxy-11beta-(4-methoxyphenyl)-19-nor-pregn-9-en-20-one is dissolved in 3 ml of 70% aqueous acetic acid and heated about 2 hours at 60° C. on a water bath. Toward the end of the reaction, the steroid begins to crystallize from the solution. By addition of water the steroid is completely precipitated and after separation is chromatographed on neutral aluminum oxide with benzene/methyl acetate (20:1). 0.146 g of the 11beta-anisyl-4,9-diene is obtained, which can be crystallized from methanol/water.

Mp: 190°-193° C. $[\alpha]_D$: 171.5°.

EXAMPLE 2

Step a) and step b) are produced as in example 1.

c)

16alpha,17alpha-Cyclohexano-11beta-(4-dimethylaminophenyl)-3,3-ethylenedioxy-5alpha-hydroxy-19-nor-pregn-9-en-20-one 0.5 ml of methyl iodide is added to a suspension of 0.48 g of magnesium shavings in 10 ml of THF and gradually mixed under argon with a solution of 4.2 g of p-bromodimethylaminobenzene in 30 ml of THF, and the internal temperature should not exceed 50° C. 15 ml is taken from the p-dimethylaminophenyl magnesium bromide solution and mixed, under cooling (−15° C.) with 0.15 g of CuCl. It is stirred for about 15 minutes with the temperature being maintained and then a solution of 0.328 g of 16alpha,17alpha-cyclohexano-3,3-ethylenedioxy-5alpha,10alpha-epoxy-19-nor-pregna-9(11)-en-2-one in 5 ml of THF is instilled. Then it is stirred for 1 hour at a temperature of about 0° C., then an aqueous ammonium chloride solution is added and the steroid is extracted with methylene chloride. After concentration by evaporation of the extracts, the residue is flash-chromatographed on basic aluminum oxide (Greiz-Doelau) with benzene/ethyl acetate (20:1). 0.4 g (94.2% of theory) of the 11-beta-dimethylaminophenyl compound, which can be recrystallized from methanol, is obtained.

Mp: 145°-149° C. $[\alpha]_D$: 31.5°.

d)

16alpha,17alpha-Cyclohexano-11beta-(4-dimethylaminophenyl)-19-nor-pregna-4,9-diene-3,20-dione 0.4 g (0.76 mmol) of 16alpha,17alpha-cyclohexano-11beta-(4-dimethylaminophenyl)-3,3-ethylenedioxy- 5alpha-hydroxy-19-nor-pregn-9-en-20-one is suspended in 5 ml of 70% aqueous acetic acid and heated for 2 hours at 60° C. water bath temperature with stirring. Thus the steroid gradually passes into solution and after completed reaction is stirred into cold water, which contains some ammonia for neutralization of the acid. The separated product is separated and flash chromatographed on neutral aluminum oxide with benzene/ethyl acetate (20:1 to 10:1). After crystallization from methanol/water 0.308 g (86.3%) of the 4,9-diene is obtained.

Mp: 121° l to 126° C. $[\alpha]_D$: 323.9°.

EXAMPLE 3 a)

16alpha,17alpha-Cyclohexano-3,3-ethylenedioxy-19-nor-pregna-5(10),9(11)-diene-20beta-ol 3.5 g of 16alpha,17alpha-cyclohexano-19-nor-pregna-4,9-dien-20beta-ol is dissolved in 75 ml of benzene and after addition of 5 ml of glycol and 0.2 g of p-toluenesulfonic acid is boiled for 2 hours on the water separator. After completed reaction, it is mixed with aqueous sodium carbonate solution and the steroid is extracted with benzene. The extracts washed neutral with water are concentrated by evaporation and crystallized from ether/n-hexane, and 3.3 g of ketal is obtained.

Mp: 130°-133° C. $[\alpha]_D$: 156°.

b)

16alpha,17alpha-Cyclohexano-3,3-ethylenedioxy-5alpha,10alpha-epoxy-19-nor-pregna-9(11)-en-20beta-ol 1.44 g of m-chloroperbenzoic acid is added with vigorous stirring to a suspension consisting of 2 g of 16alpha,17alpha-cyclohexano-3,3-ethylenedioxy-19-nor-pregna-5(10),9(11)-dien-20beta-ol in 20 ml of methylene chloride and 20 ml of a saturated aqueous sodium bicarbonate solution. After completed reaction (15 minutes) the steroid is extracted with methylene chloride, the extracts are concentrated by evaporation and the remaining residue is flash chromatographed on basic aluminum oxide (Greiz-Doelau) with toluene/ethyl acetate (10:1). 0.9 g of 5alpha,10alpha-epoxide is obtained in the form of an oil.

c)

16alpha,17alpha-Cyclohexano-3,3-ethylenedioxy-11beta-(4-methoxyphenyl)-19-nor-pregn-9-ene-5alpha-20beta-diol 5 ml is taken from 4-methoxyphenyl magnesium bromide solution prepared by reaction of 0.48 g of magnesium shavings and 2.36 ml of p-bromoanisole in 20 ml of THF at 35° C. and is mixed with 0.07 g of CuCl under argon and cooling to −5° C. to −15° C. It is stirred for 15 minutes while the cooling is maintained and then a solution of 0.765 g of 16alpha,17alpha-cyclohexano-3,3-ethylenedioxy-5-alpha,10alpha-epoxy-19-nor-pregn-9(11)-en-20beta-one in 5 ml of THF is instilled. Then it is stirred for 30 minutes at room temperature, then an aqueous ammonium chloride solution is added and the steroid is extracted with methylene chloride. After concentration by evaporation of the extracts, the residue is flash chromatographed on basic aluminum oxide (Greiz-Doelau) with benzene/ethyl acetate (4:1). After recrystallization from ether/n-hexane, 0.7 g (72.6% of theory) of the 11beta-anisyl compound is obtained.

Mp: 187°-191° C. $[\alpha]_D$: opt. inact.

d)

16alpha,17alpha-Cyclohexano-20beta-hydroxy-11beta-(4-methoxyphenyl)-19-nor-pregna-4,9-dien-3-one Production analogously to example 1 d).

Mp: 111°-116° C. $[\alpha]_D$: 91.6°.

EXAMPLE 4

The production of steps a) and b) takes place analogously to example 3.

c)

16alpha,17alpha-Cyclohexano-11beta-(4-dimethylaminophenyl)-3,3-ethylenedioxy-19-nor-pregn-9-ene-5alpha,20beta-diol 0.05 ml of methyl iodide is added to a suspension of 0.48 g of magnesium shavings in 10 ml of THF and gradually mixed under argon with a solution of 4.2 g of p-bromodimethylaminobenzene in 30 ml of THF, and the internal temperature should not exceed 50° C. 20 ml is taken from the p-dimethylaminophenyl magnesium bromide solution thus produced and mixed with 0.1 g of CuCl with cooling (−15° C.). It is stirred for about 15 minutes with this temperature being maintained and then a solution of 0.72 g of 16alpha,17alpha-cyclohexano-3,3-ethylenedioxy-5alpha,10alpha-epoxy-19-nor-pregn-9(11)-en-20beta-ol in 7 ml of THF is instilled. Then it is stirred for 3 hours at a temperature of about 0° C., then an aqueous ammonium chloride solution is added and the steroid is extracted with methylene chloride. After concentration by evaporation of the extracts, the residue is flash chromatographed on basic aluminum oxide (Greiz-Doelau) with benzene/ethyl acetate (4:1). The product can be recrystallized from methanol.

Mp: 187°-194° C. $[\alpha]_D$: 5°.

16alpha,17alpha-Cyclohexano-11beta-(4-dimethylaminophenyl)-20beta-hydroxy-19-nor-pregna-4,9-dien-3-one 0.6 g of 16alpha,17alpha-cyclohexano-11beta-(dimethylamino)-3,3-ethylenedioxy-19-nor-pregn-9-ene-5alpha,20beta-diol is reacted according to example 1d) and worked up. After crystallization from methanol/water, 0.47 g (89.3%), of the 4,9-diene is obtained.

Mp: 128°-134° C. $[\alpha]_D$: 196.8°.

EXAMPLE 5

The production of steps a) and b) takes place analogously to example 3.

16alpha,17alpha-Cyclohexano-3,3-ethylenedioxy-11-beta(4-(2'-methyl-1',3'-dioxolan-2'-yl)-phenyl-19-nor-pregn-9-ene-5alpha,20beta-diol 0.05 ml of methyl iodide is added to a suspension of 0.48 g of magnesium shavings in 13 ml of THF and gradually mixed under argon with a solution of 4.9 of p-bromo-(2'-methyl-1',3'-dioxolan-2'-yl)-benzene in 27 ml of THF, and the internal temperature should not exceed 45° C. After dissolution of the magnesium 10 ml of 4-(2'-methyl-1',3'-dioxolan-2'-yl)-phenyl magnesium bromide is taken and 0.1 g of CuCl is added to it with cooling (−5° C. to −15° C.). It is stirred for 15 minutes with this temperature being maintained and then a solution of 0.355 g of 16alpha,17alpha-cyclohexano-3,3-ethylenedioxy-5alpha,10alpha-epoxy-19-nor-pregn-9(11)-en-20beta-ol in 3 ml of THF is instilled. Then it is stirred for 1 hour, and the reaction solution is gradually brought to room temperature. After completed reaction, an aqueous ammonium chloride solution is added and the steroid is extracted with methylene chloride. After concentration by evaporation of the extracts, the remaining residue is flash chromatographed on basic aluminum oxide (Greiz-Doelau) with benzene/ethyl acetate (20:1). 0.31 g (63% of theory) of the 11-beta-acetophenyl ketal compound, which can be recrystallized from methanol, is obtained.

Mp: 194°–202° C. $[\alpha]_D$: opt. inact.

EXAMPLE 6 a)

16alpha,17alpha-Cyclohexano-3,3-ethylenedioxy-17beta-hydroxymethyl-estra-5(10), 9(11)-diene 5.9 g of 16alpha,17alpha-cyclohexano-3,3-ethylenedioxy-17beta-hydroxymethyl-estra-4,9-dien-3-one is dissolved in 100 ml of benzene and 5 ml of glycol and, after addition of 0.2 g of p-toluenesulfonic acid, is boiled for 2 hours on a water separator. After the reaction is completed, it is mixed with aqueous sodium bicarbonate solution and the steroid is extracted with benzene. The extracts, washed neutral with water, are concentrated by evaporation and crystallized from ether/n-hexane, and 5.5 g of ketal is obtained.

b)

16alpha,17alpha-Cyclohexano-3,3-ethylenedioxy-17beta-hydroxymethyl-5alpha,10alpha-epoxy-estr-9(11)-ene The production takes place analogously to example 1 step b)

Mp: acetone/n-hexane: 171°–175° C.

c)

16alpha,17alpha-Cyclohexano-3,3-ethylenedioxy-17beta-hydroxymethyl-11beta-(4-methoxyphenyl)-estr-9-en-5alpha-ol 4 ml is taken from a 4-methoxyphenyl magnesium bromide solution prepared by reaction of 0.48 g of magnesium shavings and 2.36 ml of p-bromoanisol in 20 ml of THF at 35° C. and mixed with 0.05 g of CuCl under argon and cooling to −5° C. to −15° C. It is stirred for 15 minutes with the cooling being maintained and then a solution of 0.5 g of 16alpha,17alpha-cyclohexano-3,3-ethylenedioxy-17beta-hydroxymethyl-5alpha,10alpha-epoxy-estr-9(11)-ene in 3 ml of THF is instilled. Then it is stirred for one hour at room temperature, then an aqueous ammonium chloride solution is added and the steroid is extracted with methylene chloride. After concentration by evaporation of the extracts, the residue is flash chromatographed on basic aluminum oxide (Greiz-Doelau) benzene/ethyl acetate (4:1). After recrystallization from methanol, 0.5 g (78.7% of theory) of the 11beta-anisyl compound is obtained.

Mp: 167°–171° C.

d)

16alpha,17beta-Cyclohexano-17-beta-hydroxymethyl-11beta-(4-methoxyphenyl)-estra-4,9-dien-3-one Production analogously to example 1d).

Mp: methanol/water: 114°–118° C.

EXAMPLE 7

The production of steps a) and b) takes place analogously to example 6.

c)

16alpha,17alpha-Cyclohexano-11beta-(4-dimethylaminophenyl)-3,3-ethylenedioxy-17beta-hydroxymethyl-estr-9-en-5alpha-ol 0.05 ml of methyl iodide is added to a suspension of 0.48 g of magnesium shavings in 10 ml of THF and is mixed under argon gradually with a solution of 4.2 g of p-bromodimethylaminobenzene in 30 ml of THF, and the internal temperature should not exceed 50° C. 10 ml is taken from the p-dimethylaminophenyl magnesium bromide solution thus produced and mixed with 0.1 g of CuCl with cooling (−15° C. It is stirred for about 15 minutes with this temperature being maintained and then a solution of 0.438 g of 16alpha,17alpha-cyclohexano-3,3-ethylenedioxy-17beta-hydroxymethyl-5alpha,10alpha-epoxy-estr-9(11)-ene in 3 ml of THF is instilled. Then it is stirred for 2 hours at a temperature of about 0° C., then an aqueous ammonium chloride solution is added and the steroid is extracted with methylene chloride. After concentration by evaporation of the extracts, the residue is flash chromatographed on basic aluminum oxide (Greiz-Doelau) with benzene/ethyl acetate (4:1). 0.4 g (70% of theory) of the 11beta-dimethylamino compound is obtained, which is recrystallized from ether/n-hexane.

Mp: 176°–181° C.

d)

16alpha,17alpha-Cyclohexano-11beta-(4-dimethylaminophenyl)-3,3-ethylenedioxy-17beta-hydroxymethyl-estra-4,9-dien-3-one 0.16 g of 16alpha,17alpha-cyclohexano-11beta-(4-dimethylaminophenyl)-3,3-ethylenedioxy-17beta-hydroxymethyl-estr-9-en-5alpha-ol is dissolved in 5 ml of 70% acetic acid and stirred for 2 hours at 60° C. Then the solution is mixed with water and some ammonia, after which the steroid precipitates in frittable form. The isolated crude product is flash chromatographed on neutral aluminum oxide with benzene/ethyl acetate (4:1). After crystallization from methanol/water, 0.1 g of the 4,9-diene is obtained.

Mp: 130°–134° C.

EXAMPLE 8

The production of steps a) and b) takes place analogously to example 6.

c)

16alpha,17alpha-Cyclohexano-3,3-ethylenedioxy-17-beta-hydroxymethyl-11beta-(4-(2′-methyl1,3-dioxolan-2′-yl)-phenyl)-estr-9-en-5-alpha-ol 0.05 ml of methyl iodide is added to a suspension of 0.48 g of magnesium shavings in 13 ml of THF and is gradually mixed under argon with a solution of 4.9 g of p-bromo-(2′-methyl-1,3-dioxolan-2′-yl)-benzene in 27 ml of THF, and the internal temperature should not exceed 45° C. After dissolution of the magnesium, 20 ml of 4-(2′-methyl-1′,3′-dioxolan-2′-yl)-phenyl magnesium bromide is taken and 0.15 g of CuCl is added with cooling (−5° C. to −15° C.). It is stirred for 15 minutes with this temperature being maintained and then a solution of 0.8 g of 16alpha,17alpha-cyclohexano-3,3-ethylenedioxy-17-beta-hydroxymethyl-5alpha,10alpha-epoxy-estr-9(11)-ene in 5 mol of THF is instilled. Then it is stirred for 3 hours, and the reaction solution is gradually brought to room temperature. After the reaction, an aqueous ammonium chloride is added and the steroid is extracted with methylene chloride. After concentration by evaporation of the extracts, the remaining residue is chromatographed on basic aluminum oxide (Greiz-Doelau) with benzene/ethyl acetate. 0.75 g (67% of theory) of the 11-beta-acetophenyl ketal compound is obtained, which can be recrystallized from methanol.

Mp: 199°-204° C. $[\alpha]_D$: −10.7°.

d)

11beta-(4-Acetylphenyl)-16alpha,17alpha-cyclohexano-17beta-hydroxymethyl-estra-4,9-diene-3-one The production takes place analogously to example 1 d).

Mp: methanol/water: 132°-137° C.

EXAMPLE 9 a)

16alpha,17alpha-Cyclohexano-3,3-ethylenedioxy-17beta-formyl-estra-5(10),9(11)-diene 0.7 g of 16alpha,17alpha-cyclohexano-3,3-ethylenedioxy-17-beta-hydroxymethyl-estra-5(10),9(11)-diene is dissolved in 20 ml of methylene chloride and mixed with 0.9 g of sodium acetate (anhydrous), 0.9 g of dried and pulverized molecular sieve as well as 0.9 of pyridinium chlorochromate. It is stirred for about 1 hour at room temperature and the suspension is then filtered on basic aluminum oxide. After elution with methylene chloride, 0.65 g of the 11beta-formyl compound is obtained as oil.

b)

16alpha,17alpha-Cyclohexano-3,3-ethylenedioxy-17-beta-formyl-5alpha,10alpha-epoxy-estr-9-ene The production takes place analogously to example 1 b).

$^3$H NMR [ppm]: 9.6 (1H, CHO); 5.99 (1H, vinyl); 3.01 (4H, ketal); 0.78 (3H, 13 Me).

c)

16alpha,17alpha-Cyclohexano-3,3-ethylenedioxy-17beta-formyl-11-beta-(4-methoxyphenyl)-estr-9-en-5alpha-ol 4 ml is taken from a 4-methoxyphenyl magnesium bromide solution prepared by reaction of 0.49 g of magnesium shavings and 2.36 ml of bromoanisol in 20 ml of THF at 35° C. and mixed with 0.5 g of CuCl under argon and cooling to −5° C. to −15° C. It is stirred for 15 minutes with the cooling being maintained and then a 0.12 g of product enriched with 16alpha,17alpha-cyclohexano-3,3-ethylenedioxy-17beta-formyl-5alpha,10alpha-oxido-estr-9(11)-ene in 7.5 ml of THF is instilled. Then it is stirred for one hour at room temperature, then an aqueous ammonium chloride solution is added and the steroid is extracted with methylene chloride. After concentration by evaporation of the extracts, the residue is flash chromatographed on basic aluminum oxide (Greiz-Doelau) benzene/ethyl acetate. A benzene/ethyl acetate mixture (20:1) is used as mobile phase. After recrystallization from methanol, 0.05 g (32.7 of theory) of the 11beta-anisyl compound is obtained.

Mp: 170°-172° C. $[\alpha]_D$: 3.3°.

d)

16alpha,17alpha-Cyclohexano-3,3-ethylenedioxy-17beta-formyl-11beta-(4-methoxyphenyl)-ester-9an-5alpha-ol 0.1 g of 16alpha,17alpha-cyclohexano-3,3-ethylenedioxy-17beta-hydroxymethyl-11beta-(4-methoxyphenyl)-estr-4-en-5alpha-ol is dissolved in 10 ml of methylene chloride and mixed with 0.2 g of sodium acetate, 0.5 g of dried and pulverized molecular sieve as well as 0.3 g of pyridinium chlorochromate. It is stirred for about 1 hour at room temperature, then filtered from the solid components, diluted with water and the steroid is extracted with methylene chloride. After preparative layer chromatography on silica gel, a benzene/ethyl acetate mixture (1:1) is used as mobile phase, 0.88 g (80% of theory) of the anisyl compound is obtained by crystallization from methanol.

EXAMPLE 10

The production of steps a) and b) takes place analogously to example 9.

c)

16alpha,17alpha-Cyclohexano-11beta-(4-dimethylaminophenyl)-3,3-ethylenedioxy-17beta-formyl-estr-9-en-5alpha-ol 0.05 ml of methyl iodide is added to a suspension of 0.48 g of magnesium shavings in 10 ml of THF and is mixed under argon gradually with a solution of 4.2 g of p-bromodimethylaminobenzene in 30 ml of THF, and the internal temperature should not exceed 50° C. 11.5 ml is taken from p-dimethylaminophenyl magnesium bromide solution thus produced and mixed with 0.065 g of CuCl with cooling (−15° C.). It is stirred for about 15 minutes with this temperature being maintained and then a solution of 0.41 g of a product enriched with 16alpha,17alpha-cyclohexano-3,3-ethylenedioxy-17beta-formyl-5alpha,10alpha-oxido-estr-9(11)-ene in 3 ml of THF is instilled. Then it is stirred for 3 hours at a temperature of about 0° C., then an aqueous ammonium chloride solution is added and the steroid is extracted with methylene chloride. After the concentration by evaporation of the extracts, the residue is flash chromatographed on basic aluminum oxide (Greiz-Doelau). A benzene/ethyl acetate mixture (20:1) is used as mobile phase. 0.2 g (37.5% of theory) of the 11beta-dimethylamino compound is obtained, which can be recrystallized from methanol.

Mp: 165°-168° C. $[\alpha]_D$: opt. inact.

d)

16alpha,17alpha-Cyclohexano-11beta-(4-dimethylaminophenyl)-17beta-formyl-estra-4,9-dien-3-one 0.2 g of 16alpha,17alpha-cyclohexano-11-beta-(4-dimethylaminophenyul)-3,3-ethylenedioxy-17beta-formyl-estr-9-en-5alpha-ol is treated according to example 1d). After chromatography, 0.15 g of the 4,9-diene is obtained, which can be crystallized from methanol/water.

Mp: 113°-116° C. $[\alpha]_D$: 197.8°.

EXAMPLE 11

The production of steps a) and b) takes place analogously to example 9.

c)

16alpha,17alpha-Cyclohexano-3,3-ethylenedioxy-17beta-formyl-11beta-(4-(2'-methyl-1,3-dioxolan-2'-yl)-phenyl-19-nor-pregna-9-en-5alpha-ol 0.05 ml of methyl iodide is added to a suspension of 0.48 g of magnesium shavings in 18 ml of THF and is mixed under argon gradually with a solution of 4.9 g of p-bromo-(2-methyl-1,3-dioxolan-2'-yl) benzene in 27 ml of THF, and the internal temperature should not exceed 45° C. After dissolution of the magnesium, 18 ml of 4-(2'-methyl-1',3'dioxolan-2'-yl)-phenyl magnesium bromide is taken and 0.1 g of CuCl is added to it with cooling (−5° C. to −15° C). It is stirred for 15 minutes with this temperature being maintained and then a solution of 0.4 g of 16alpha,17alpha-cyclohexano-3,3-ethylenedioxy-17-beta-formyl-51 alpha,10alpha-oxido-estr-9(11)-ene in 3 ml of THF is instilled. Then it is stirred for 2 hours and the reaction mixture is gradually brought to room temperature. After completed reaction, an aqueous ammonium chloride solution is added and the steroid is extracted with methylene chloride. After the concentration by evaporation of the extracts, the residue is chromatographed on basic aluminum oxide (Greiz-Doelau). A benzene/ethyl acetate mixture is used as mobile phase. 0.39 g (64.9% of theory) of the 11beta-acetophene ketal compound is obtained, which can be recrystallized from methanol.

Mp: 201°-206° C. $[\alpha]_D$: opt. inact.

We claim:

1. An 11β-Aryl-16α,17α-cyclohexano-estra 4,9-diene of formula I

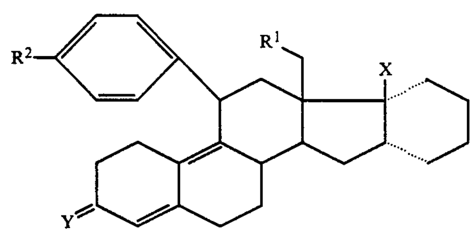

wherein $R^1$ is H or a methyl group;

$R^2$ is $—OCH_3$, $—SCH_3$, $—N(CH_3)_2$, $—NHCH_3$, —CN, —CHO, $—COCH_3$ or $—CHOHCH_3$;

X is —CHO, $—COCH_3$, $—CH_2OH$, $—CHOHCH_3$, $—CH_2CHO—C_{1-7}$-alkyl, $—CH_2CHO—C_{1-7}$-alkanoyl, $—CH_2O—C_{1-7}$-alkyl, $—CH_2O—C_{1-7}$-alkanoyl, $—COO—C_{1-7}$-alkyl, $CH_3CH_2—$, $—CH_3$, —COOH or —CN, and Y is =O, =NOH, $=NOCH_3$ or a cyclic thioketal having 2 or 3 ring atoms.

2. A compound of claim 1, wherein $R^1$ is H, $R^2$ is —OCH·, $—N(CH_3)_2$, —CHO or $—COCH_3$, X is —CHO, $—COCH_3$, $—CH_2OH$ or —CHOHCH·, and Y is =O or =NOH.

3. Compounds of general formula I, namely

16alpha,17alpha-cyclohexano-11beta-(4-methoxyphenyl)-19-nor-pregna-4,9-diene-3,20-dione, 16alpha,17alpha-cyclohexano-11beta-(4-dimethylaminophenyl)-19-nor-pregna-4,9-diene-3,20-dione, 16alpha,17alpha-cyclohexano-20beta-hydroxy-11beta-(4-methoxyphenyl)-19-nor-pregna-4,9-diene-3,20-dione, 16alpha,17alpha-cyclohexano-11beta-(4-dimethylaminophenyl)-20beta-hydroxy-19-nor-pregna-4,9-diene-3,20-dione, 16alpha,17alpha-cyclohexano-17beta-hydroxymethyl-11beta-(4-methoxyphenyl-estra-4,9-dien-3-one, 16alpha,17-alpha-cyclohexano-11beta-(4-dimethylaminophenyl)-17-beta-hydroxymethyl-estra-4,9-diene-3-one, 11beta-(4-acetylphenyl)-16alpha,17alpha-cyclohexano-17beta-hydroxymethyl-estra-4,9-dien-3-one or, 16alpha,17alpha-cyclohexano-11beta-(4-dimethylaminophenyl)-17beta-formyl-estra-4,9-dien-3-one, each a compound of claim 1.

4. A compound of formula V

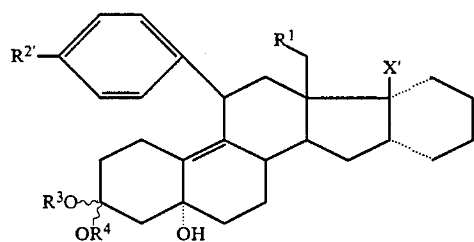

wherein $R^1$ is H or a methyl group;

$R^{2'}$ is $—OCH_3$, $—SCH_3$, $—N(CH_3)_2$, $—NHCH_3$, —CN, —CHO, $—COCH_3$ or $—CHOHCH_3$;

X' is —CHO, $—COCH_3$, $—CH_2OH$, $—CHOHCH_3$, $—CH_2CHO—C_{1-7}$-alkyl, $—CH_2CHO—C_{1-7}$-alkanoyl, $—CH_2O—C_{1-7}$-alkyl, $—CH_2O—C_{1-7}$-alkanoyl, $—COO—C_{1-7}$-alkyl, $CH_3CH_2—$, $—CH_3$, —COOH or —CN; and $R^3$ and $R^4$ each is a methyl or ethyl group or together are an ethylene group or 2,2-dialkylpropylene group and wherein any keto groups are optionally protected by ketal groups.

5. A pharmaceutical preparation comprising an effective amount of a compound of of claim 1 and a pharmaceutically acceptable excipient.

6. A method of inducing labor, comprising administering to a pregnant patient an effective amount of a compound of claim 1.

7. A method of inducing abortion, comprising administering to a pregnant patient an effective amount of a compound of claim 1.

8. A method of treating endometriosis, comprising administering to a patient an effective amount of a compound of claim 1.

9. A method of treating dysmenorrhea, comprising administering to a patient an effective amount of a compound of claim 1.

10. A method of treating endocrine hormone-dependent tumors, comprising administering to a patient an effective amount of a compound of claim 1.

11. A method of inducing an antigestagenic effect in a patient, comprising administering an effective amount of a compound of claim 1.

* * * * *

UNITED STATES PATENT AND TRADEMARK OFFICE
CERTIFICATE OF CORRECTION

PATENT NO. : 5,166,199

DATED : November 24, 1992

INVENTOR(S) : Helmut Kasch et al.

It is certified that error appears in the above-identified patent and that said Letters Patent is hereby corrected as shown below:

Column 13

Claim 3, line 68; delete "e" in diene. Should read --dien--

Claim 3, Col. 14, line 2; delete "e" in diene. Should read --dien--

Claim 3, Col. 14, line 6; delete "e" in diene. Should read --dien--

Claim 3, Col. 14, line 9; delete "e" in diene. Should read --dien--

Col. 14, line 14, Claim 3; delete "e" in diene. Should read --dien--

Signed and Sealed this

Twenty-third Day of November, 1993

Attest:

BRUCE LEHMAN

Attesting Officer

Commissioner of Patents and Trademarks